United States Patent [19]

Fahy

[11] Patent Number: 5,707,971
[45] Date of Patent: Jan. 13, 1998

[54] MODULATION OF GLYCOLYTIC ATP PRODUCTION

[75] Inventor: Gregory M. Fahy, Gaithersburg, Md.

[73] Assignees: Life Resuscitation Technologies, Inc.; Organ, Inc., both of Chicago, Ill.

[21] Appl. No.: 476,035

[22] Filed: Jun. 7, 1995

[51] Int. Cl.$^6$ .......................... A61K 31/70; A61K 31/115
[52] U.S. Cl. .................... 514/43; 514/45; 514/694
[58] Field of Search ................. 514/43, 45, 694, 514/23

[56] References Cited

U.S. PATENT DOCUMENTS

| | | | |
|---|---|---|---|
| 4,546,095 | 10/1985 | Markov | 514/23 |
| 4,703,040 | 10/1987 | Markov | 514/23 |
| 4,757,052 | 7/1988 | Markov | 514/23 |
| 5,039,665 | 8/1991 | Markov | 514/23 |
| 5,395,822 | 3/1995 | Izumi et al. | 514/3 |

OTHER PUBLICATIONS

The Merck Index, 12th Edition, Merck & Co., Inc., Whitehouse Station, NJ., Nos. 2531, 4491 and 6429, pp. 417, 418, 763 and 1088, 1966.

*Primary Examiner*—John W. Rollins
*Attorney, Agent, or Firm*—Oliff & Berridge, P.L.C.

[57] ABSTRACT

Delivery of fuel and cofactors augments ATP production in cells, and mitigates damages in ischemic or metabolically impaired tissues. The processes may be particularly effective in acute or chronic ischemic conditions, for reversing anesthesia, for treating diabetes, for producing or preventing coma due to lack of fuel or ATP, for reversing processes of aging, as dietary supplements, as performance enhancers, for example, in sports, for tissue transplantation and other surgery, and for cold storage or cryopreservation of tissues such as organs.

43 Claims, No Drawings

MODULATION OF GLYCOLYTIC ATP PRODUCTION

BACKGROUND OF THE INVENTION

The production of ATP (adenosine triphosphate) is essential for cellular energy metabolism. Cellular ATP production can take place either during glycolysis or during mitochondrial processing of the pyruvate which results from glycolysis. Glycolysis is therefore necessary for the production of ATP from sugars under both aerobic and anaerobic conditions. Since ATP is essential to continued cell function, when aerobic metabolism is slowed or prevented by lack of oxygen, for example, by hypoxia or anoxia due to anemia, deficient oxygen supply or ischemia, anaerobic pathways for producing ATP are stimulated and become critical for maintaining viability.

The first stage of glycolysis involves the transformation of glucose into fructose 1,6-bisphosphate (FBP). This transformation requires using two molecules of ATP per molecule of glucose converted to FBP. Exogenously supplied FBP is thus a more energetically advantageous substrate than glucose.

Production of pyruvate from glucose or FBP yields four molecules of ATP per molecule of glucose or FBP. Thus, in anaerobic metabolism, a molecule of FBP has a net yield of twice the number of ATP molecules as does a molecule of glucose.

Another advantage of using FBP over using glucose in metabolism results from decreased pH caused by ischemia or hypoxia. When aerobic pathways are not available to metabolize pyruvate, pyruvate and lactate (and their acids) accumulate in cells, causing an increased concentration of hydrogen ions (a decreased pH). Conversion of glucose to FBP is inhibited by a low pH, but the conversion of FBP to pyruvate is not strongly pH dependent. Glucose transport into cells is also inhibited by a low pH.

U.S. Pat. Nos. 4,546,095, 4,703,040, 4,757,052 and 5,039,665 to Markov recognize advantages of FBP as an alternate energy source to glucose for conditions in which ischemic or hypoxic conditions have compromised ATP production.

In order to complete the conversion of pyruvate to $CO_2$ and water, thereby producing large amounts of ATP, oxygen is required. Pyruvate therefore does not act as an energy source during anoxia, for example, anoxia resulting from ischemia.

U.S. Pat. No. 5,395,822 to Izumi has recently described that the presence of pyruvate during ischemia allows the hippocampus to retain better integrity after reoxygenation than does the presence of glucose. One explanation of this phenomenon is that the decreased pH resulting from the ischemia inhibits metabolism of glucose to pyruvate. However, when oxygen is re-introduced, the presence of exogenous pyruvate provides a pool of pyruvate for use by the mitochondria independent of the acid inhibition of glycolysis.

Both FBP and pyruvate have been found beneficial in restoring ATP generation capabilities following periods of ischemia. However, alternate therapies for regenerating ATP production capability could provide critically needed flexibility for a clinician treating idiosyncratic patients, and alternate therapies that work better than FBP or pyruvate could save and improve lives. Also because various cell types and the blood brain barrier will vary in permeabilities to different molecules, substrates other than FBP and pyruvate are desirable.

SUMMARY OF THE INVENTION

This invention relates to the augmentation or maintenance of cellular ATP levels. The ATP augmenting chemicals and methods of the present invention stimulate glycolysis and mitochondrial metabolism by providing fuel and/or cofactors necessary for the production of ATP either anaerobically or aerobically. These chemicals can be delivered to a tissue, for example, an organ or an intact organism such as a person, e.g., in vitro or in vivo, to maintain or provide for ATP synthesis when aerobic ATP synthesis is or has been compromised. The compounds and uses of the invention may be useful for reducing or preventing tissue damage in acute or chronic ischemia, for reversing anesthesia, for treating diabetes, for reversing or preventing coma due to lack of fuel or ATP, for reversing processes of aging, for use as dietary supplements, or as performance enhancers, for example, in sports, for tissue transplantation and other surgery, involving ischemic and/or hypoxic or anoxic conditions and for cold storage or cryopreservation of organs.

DETAILED DESCRIPTION OF PREFERRED EMBODIMENTS

Inter alia, the instant invention solves problems associated with restoring normal metabolism after metabolism has been slowed or stopped. Metabolism can be slowed or stopped in several ways including chemical, for example, decreased pH, or more specific inhibitors such as anesthetics, deprivation of oxygen, for example, by anemia, carbon monoxide poisoning, slowing or stopping circulation, and decreased temperature. The invention provides methods and compositions for maintaining or restoring metabolism during or following such a metabolic crisis.

The metabolism of glucose to carbon dioxide and water has been studied extensively and chemical compounds in the pathway are well known. To date, however, the chemical compounds of the present invention have not been put to use for the purposes of the present invention.

G3P

The invention embodies administration of glyceraldehyde 3-phosphate (G3P) to a tissue as a glycolytic substrate. G3P has a lower molecular mass and less charge than FBP. G3P therefore can penetrate cells more rapidly than FBP. Another advantage of G3P over FBP is that G3P is farther along in glycolysis than FBP, and therefore may be effective when FBP would be ineffective due to inhibition of any of the bypassed enzymes necessary for conversion of FBP to G3P, yet the G3P made from FBP retains all the ATP-generating potential of the parent molecule.

Dihydroxyacetone phosphate, the metabolic intermediate immediately upstream of G3P, and 1,3-diphosphoglycerate, the metabolic intermediate immediately downstream of G3P, are too unstable to be of practical use. Since each FBP molecule is split to produce two G3P molecules, twice as much G3P as FBP should nominally be present on a molar basis when using G3P to replace FBP in restoring metabolism. As described below, however, G3P is often comparable to FBP when given in doses no greater than or even less than doses of FBP.

$NAD^+$

Another chemical required for the metabolism of FBP or G3P to ATP is the cofactor, $NAD^+$. $NAD^+$ is usually present at low concentrations within the cell. During metabolism G3P is oxidized to 3-phosphoglycerate (3-PG) as $NAD^+$ is reduced to NADH. In order to regenerate $NAD^+$, NADH reduces pyruvate to lactate. The regenerated $NAD^+$ is then available to oxidize G3P to keep the ATP generation process functioning.

This NADH/NAD$^+$ cycle has three deleterious results. First, lactic acid, a metabolic inhibitor, accumulates within the cell as a result of reduction of pyruvate by NADH. Second, pyruvate, which could otherwise be used to provide ATP, is made temporarily unavailable due to conversion to lactate. Third, when all of the accumulated lactate is suddenly converted into pyruvate upon reoxygenation, the NAD$^+$ consumed in the process could temporarily limit glycolysis.

The invention provides compositions and methods for delivering NAD$^+$ to tissues, for example in an organ or person. Delivery can be accomplished through, for example, a perfusing or bathing solution, an IV solution, an injectable supplement or a food supplement containing the composition being provided to the afflicted area or person in liquid or solid forms.

While not wishing to be bound by any theory, supplementing cells with NAD$^+$ has at least the following advantages: first, it makes more pyruvate available to the mitochondria immediately upon reoxygenation since less cycling of NADH/NAD$^+$ will convert less pyruvate to lactate during hypoxia; second, by minimizing the lactate pool, the depletion of cytoplasmic NAD$^+$ upon reoxygenation due to the oxidation of lactate back to pyruvate will be minimized, thereby conserving NAD$^+$ for the promotion of glycolysis; third, the NADH accumulated because of reduced conversion to NAD$^+$ by lactate production is immediately available for oxidation by the electron transport chain when oxygen is reintroduced; fourth, the conserved NADH may also participate in anabolic reactions; fifth, since NAD$^+$ is used in multiple cell pathways and may be depleted under ischemic and other conditions, supplementing with NAD$^+$ will correct any such deficiencies; and sixth, given that NAD$^+$ concentrations in cells tend to be low, the effectiveness of any exogenous glycolytic substrate that requires NAD$^+$ for its oxidation, including glucose, FBP and G3P, may be limited by a limited NAD$^+$ supply unless exogenous NAD$^+$ is provided along with the added substrate.

The invention also includes providing compositions comprising NAD$^+$. Because NAD$^+$ is required for metabolism of either FBP or G3P to produce ATP, the combination of NAD$^+$ and FBP or the combination of NAD$^+$ and G3P delivered to tissue, for example in a metabolically deficient tissue, is more effective than adding FBP or G3P or NAD$^+$ alone.

3-PG and 2-PG

The invention further comprises augmenting generation of ATP with 3-phosphoglycerate (3-PG). 3-PG is a reaction product of G3P. 3-PG occurs downstream of G3P in the metabolic pathway after the consumption of NAD$^+$ and the production of 1 ATP. 3-PG is capable of producing 1 ATP, but requires no NAD$^+$ and produces no NADH. Because no NADH is made, pyruvate made from the addition of 3-PG is not further metabolized into lactic acid. Instead, all the 3-PG metabolized under anaerobic conditions must end up as pyruvate which is ready for oxidation by the mitochondria. Since no lactate is generated in this process, the inhibition due to lactate and the cycling of NADH/NAD$^+$ are avoided. Thus, embodiments of the invention comprise delivering a composition comprising 3-PG to tissue such as tissue in a metabolically deficient state.

The compound following 3-PG in the glycolytic pathway, 2-phosphoglycerate (2-PG), is less stable and thus less suitable for practical use. Because either 2-PG or 3-PG produce only 1 ATP molecule, as compared to 2 ATP molecules produced by each G3P, twice as much 2-PG or 3-PG as G3P should be used.

2,3-DPG

A conversion of 3-PG to 2-PG is necessary for the production of ATP from 3-PG. 2,3-diphosphoglycerate (2,3-DPG) catalyzes the conversion of 3-PG to 2-PG and is therefore useful, especially in combination with 3-PG. The conversion reaction of 3-PG to 2-PG consumes no ATP molecules. However, the formation of 2,3-DPG by the cell requires ATP and thus in ischemic conditions, where ATP is in short supply, providing 2,3-DPG will conserve ATP for other cellular purposes.

Since the metabolism of either FBP or G3P has as an intermediate 3-PG, providing 2,3-DPG in addition to either FBP or G3P will likewise help to conserve ATP molecules. The invention therefore embodies supplementing a metabolically deficient tissue with 2,3-DPG to help glycolysis to proceed, for example when endogenous 2,3-DPG is unavailable, perhaps due to lack of ATP.

Since either NAD$^+$ or 2,3-DPG could be rate limiting, bottlenecks of the glycolytic pathway may be avoided by providing both of these compounds concurrently. The invention provides compositions including these compounds and delivery of these compositions to tissue, for example to a metabolically deficient person or in vitro tissue.

The invention also encompasses compositions and administration of FBP or G3P with NAD$^+$ and 2,3-DPG. When FBP and G3P are also provided along with NAD$^+$ and 2,3-DPG, glycolysis will not be impeded by lack of substrate or by limitations of these cofactors.

Phosphoenol Pyruvate (PEP)

The compound that follows 2-PG in the glycolytic pathway is phosphoenol pyruvate (PEP). PEP gives rise to the second ATP produced in glycolysis and is sufficiently stable to be practical to use. The present invention embodies this use by administrating PEP to tissue. For example, 2,3-DPG is not required for the conversion of PEP to pyruvate. The invention thus comprises delivering PEP to tissue, especially wherever or whenever 2,3-DPG is limiting or the enzymes that convert 3-PG to PEP are inhibited. Similar to 3-PG, PEP will not consume NAD$^+$ and NADH will not be produced. PEP is therefore a particularly advantageous substrate. Metabolism of PEP to pyruvate also produces 1 ATP molecule, so 2 PEP molecules will replace 1 G3P molecule or 1/2 FBP or glucose molecule.

Pyruvate with FBP

FBP can also be used in conjunction with pyruvate, one of its metabolites. This combination as used in the present invention can be especially useful in an intraischemic treatment approach, for example, treatment of brain tissue after the onset of ischemic insult but before reoxygenation. When used intra-ischemically, the FBP component of the combination will allow ATP production to begin immediately, before reoxygenation, while the added pyruvate will be immediately available to the citric acid cycle once oxygen is reintroduced. Practicing the invention by using this composition comprising FBP and pyruvate to treat brain ischemia should provide greater assurance of hippocampal protection than the use of FBP alone.

Since significant quantities of FBP can be converted into lactate, the invention's provision of an exogenous pyruvate pool will avoid the need for lactate to be converted back to pyruvate for mitochondrial metabolism to produce ATP in the citric acid cycle. The pyruvate pool will also conserve NAD$^+$, thereby avoiding inhibition of FBP oxidation due to the necessary conversion of lactate into pyruvate for use by mitochondria.

In treatment of a complex tissue, organ or organism according to the invention, the combination of FBP and pyruvate offers a further advantage in that cells relatively impermeable to either FBP or pyruvate will gain protection from the presence of the alternate fuel source.

Co-enzyme A

Before pyruvate can be utilized in the citric acid cycle it must be combined with coenzyme A (CoA) to form acetyl Coenzyme A (acetyl CoA). Coenzyme A irreversibly reacts with pyruvate, preventing its conversion to lactate. Although CoA is nominally impermeable, the inventor has found that CoA improves hypothermically stored organs and improves ion pumping in kidney slices. This predicts that CoA can penetrate cells and mitochondria under conditions of deep hypothermia. CoA penetration during periods of ischemia at temperatures closer to normal metabolic temperatures allows pyruvate to be irreversibly converted to acetyl CoA in the mitochondrial matrix. Less lactate will therefore be produced. $NAD^+$ otherwise used for conversion of lactate to pyruvate will be conserved for other purposes. At the same time, the mitochondria will be primed by the presence of acetyl CoA for rapid ATP production upon reoxygenation. This invention thus provides for delivering CoA to a tissue to protect tissues or cells thereof from death, by augmenting ATP production during and after ischemia, while also sparing $NAD^+$ for other metabolic purposes.

$NAD^+$ Plus CoA and Other Combinations

Under ischemic conditions, the reaction between pyruvate and CoA to form acetyl CoA consumes $NAD^+$. The invention therefore provides a composition including CoA and $NAD^+$ for delivery to tissue, for example to an ischemic individual or organ. $NAD^+$ is necessary for ATP production, for example, from oxidation of G3P under anaerobic conditions. Delivering CoA plus $NAD^+$ will avoid depletion of $NAD^+$. As an extra advantage, since both cofactors, $NAD^+$ and CoA, each inhibit lactate accumulation, this combination of the cofactors is especially effective in preventing lactate accumulation.

CoA and $NAD^+$ are effective at producing ATP when substrate fuel is present. Thus a combination of CoA with $NAD^+$, and a fuel source, for example G3P, is especially preferred. Another composition and method embodied in the invention therefore comprises providing a composition including $NAD^+$, CoA and a fuel source such as G3P to prevent lack of cofactors or fuels from limiting ATP production.

CoA plus $NAD^+$ plus Carnitine

Ischemia leads to the release of free fatty acids from cell membranes into the cytoplasm or extracellular matrix. Fatty acids can participate in reperfusion injury through conversion to inflammatory mediators as well as through lipid peroxidation related damage to cells once oxygen supply is reestablished. By restoring fatty acids to membranes or by promoting the activation of these fatty acids and providing for their translocation to mitochondria, this toxicity may be avoided. To improve ATP metabolism following hypoxia or ischemia, embodiments of the invention involve delivering CoA to accomplish, among other functions, removal of damaging fatty acids from the cytoplasm.

CoA is used for intracellular transport and activation of fatty acids for subsequent metabolism. Fatty acids are activated on the outer mitochondrial membrane by the formation of fatty acyl CoA. The fatty acyl group is then transferred to carnitine and the complex then crosses the inner mitochondrial membrane to the matrix area where lipid metabolism proceeds. CoA thus mitigates ischemic damage by removing proinflammatory, peroxidizable lipids from the cytoplasm while also contributing to aerobic ATP production by facilitating delivery of fatty fuels to mitochondria.

The invention, through delivery of CoA for fatty acid removal and thereby lessening or minimizing production of inflammatory hormones, such as prostaglandins, from fatty acids also contributes a longer term anti-inflammatory effect for protecting afflicted tissues.

Carnitine, in the form of acetyl-carnitine, has been shown to be beneficial in reversing ischemic damage by binding fatty acids and transporting them to the mitochondria. However, acetyl-carnitine is converted to carnitine in the body. The invention thus includes delivering acetyl-carnitine and/or carnitine with other compounds to facilitate transport of fatty acids to the mitochondria matrix for conversion to acetyl CoA. Providing carnitine to ischemic regions, for example 1-10 mM carnitine or acetyl carnitine, in a wash or IV solution, can help mitigate ischemic damage by participating in removal of fatty acids and thereby have effects similar to or effects synergistic with CoA.

The value of CoA and $NAD^+$ in facilitating this function of carnitine through provision of properly activated fatty acids has not been previously suggested. Providing carnitine or acetyl-carnitine alone may have limited effectiveness due to the slowness or absence of the required activation of fatty acids before their transport across the inner mitochondrial membrane. The invention thus provides for delivery of a composition containing $NAD^+$, carnitine and CoA to a metabolically deficient person or tissue. Providing a combination of $NAD^+$ and carnitine or acetyl-carnitine therefore provides $NAD^+$ for activation of the fatty acid and a carnitine compound for translocation to the mitochondrial matrix. The combination thus increases the effectiveness in reversing ischemic damage over provision of either compound alone. Once again, mitochondria will be primed, this time by the presence of activated fatty acids, for production of ATP upon reoxygenation.

The invention by providing both $NAD^+$ and CoA for activating fatty acids, and a carnitine compound for transporting fatty acids into mitochondria helps prevent toxic effects of fatty acids and provides a fuel source for mitochondrial use once oxygen supply is reestablished.

Acetyl COA

Since most fuel molecules enter the citric acid cycle as acetyl CoA, direct provision of acetyl CoA may also be advantageous as a fuel source. This substrate will then be available for utilization in the citric acid cycle immediately upon reoxygenation. Since the formation of acetyl CoA from either pyruvate or fatty acids requires $NAD^+$, numerous enzymes, coenzymes, and a redox cycle involving the formation and breakage of disulfide bonds at the active site of one of the enzymes, direct provision of acetyl CoA may avoid metabolic bottlenecks due to an insult to any one or more of these systems, for example, an insult resulting from a chemical or ischemic attack.

Therefore, delivery of exogenous acetyl CoA according to the invention provides immediate access to acetyl CoA for production of ATP upon reoxygenation. Delivery of acetyl CoA according to the invention may be carried out as an alternative to delivery of pyruvate for any application in which pyruvate may be useful, for example, salvage of hippocampal neurons or other tissues after an ischemic insult. Acetyl CoA may have fewer side effects than CoA alone, since the energy consuming reactions of CoA alone will not be possible from acetyl CoA until after energy has been produced in the form of ATP from the oxidation of acetyl CoA.

pH Buffering and $H^+$ exchange Inhibitors

During compromised metabolism, for example, during ischemic conditions, a decrease in pH often occurs, and the altered pH impacts the activities of many of the enzymes necessary for metabolism. Embodiments of the invention modulate ATP production by maintaining a higher (more normal) pH in the tissue by bathing or perfusing an afflicted tissue with a biocompatible buffer. Buffering these pH changes, for example, by providing biocompatible buffers such as HEPES (N-2-hydroxyethylpiperidine-N'-2-ethanesulfonic acid) or THAM (2-amino-2-hydroxymethyl-1,3-propanediol), will reduce or prevent pH related inhibition of metabolism. This buffering approach can be used to augment the effectiveness of any of the resuscitation scenarios described herein as well as most other resuscitation scenarios. An effective range of buffering capacity is approximately equivalent to 3 to 50 mM HEPES and can be determined for each buffer, for example, by reference to literature or by routine experimentation.

A poorly understood process known as the pH paradox has been observed wherein restoring pH to normal levels immediately following ischemia is associated with increased damage to the ischemic tissue. When pH buffering is used to maintain or restore extracellular pH during ischemia, dimethyl amiloride (1–10 μM) is preferably added to, for example, the buffered perfusate, IV fluid, lavage, or bath to diminish or eliminate effects associated with the pH paradox. By elevating extracellular pH while slowing a rise in intracellular pH using $Na^+/H^+$ exchange inhibitor, intracellular pH will rise at the maximum rate compatible with avoidance of the pH paradox. During this interval, provision of an anaerobic ATP-producing substrate, for example, FBP, G3P or PEP plus cofactors, for example, $NAD^+$ and CoA, will sustain ATP production while intracellular pH remains low.

Situational Examples

Compounds and compositions described herein for maintaining and augmenting ATP production and preventing accumulation of harmful substance will be most advantageous when given during continuing conditions of limited oxygen supply or effectiveness, e.g., under conditions such as drowning, hemorrhagic shock, cardiac arrest or mitochondrial poisoning with agents such as cyanide.

In most such situations, immediate restoration of full tissue oxygenation cannot be accomplished quickly, and cyanide poisoning cannot be reversed immediately. Therefore a therapeutic window for improving a patient's energy metabolism generally appears between the time a patient can be treated and the time oxidative metabolism can be restored by improving tissue oxygenation and/or removing poisons that interfere with energy metabolism.

Although ischemic attacks often occur without warning, there are many instances of planned ischemia, for example, ischemia necessary for organ transplantation. The invention provides for greater transplantation success, either by increased survival of an organ or improved function of an organ after transplantation by modulating ATP production in the donor organ during its ischemic period. The donor organ can be treated by perfusion, washing and/or bathing with ATP augmentation compounds or compositions of the invention, before removal of an organ from the donor and/or before transplantation into the host.

The invention embodies uses of compositions and compounds of the invention before and/or during cryopreservation or cold storage, during transport, and/or during and/or after surgery. The viability of tissue during and following storage will be improved. Return of function after reperfusion will also be accelerated.

Cryopreservation

Cryopreservation often causes generalized cellular damage that must be repaired by energy dependent mechanisms. Methods of the invention provide cofactors and substrates for maintenance of ATP levels critical to repairing cryopreservation induced damage. Anabolic activity necessary to repair cryopreservation damage also requires NADH. The ATP augmentation and maintenance compounds and compositions of the present invention, especially those conserving NADH, are especially useful for reversing or avoiding ischemic injury and hypothermic organ preservation damage, as well as cryopreservation damage.

Reversing Anesthesia

The invention is also useful for reversal of effects of anesthesia. Restoration of normal metabolism is essential for reversing anesthetic effects. The compounds, compositions and methods described herein are useful for reversing anesthesia, for example, barbiturate induced anesthesia or Hypnorm induced anesthesia, by increasing the metabolic supply of ATP.

Prolonged Storage of Blood

Presently, the most commonly transplanted tissue is blood. Several modalities have been developed for preserving blood up to several weeks or months in an unfrozen condition. In these modalities, conditions that stimulate cellular synthesis of ATP and 2,3-DPG have been found to extend the useful transplantable shelf life of blood. The invention embodies methods that improve storage of blood and blood products by providing solutions and combinations of ATP augmenting agents described herein to provide superior ATP maintenance results over those obtained using existing solutions.

Since red blood cells (RBCs) have no mitochondria, the compounds and compositions described herein which involve only mitochondrially mediated benefits will only be useful for non-RBC cellular blood products. The non-mitochondrial effects, however, will serve to maintain ATP levels in stored blood which includes RBCs. Thus admixing of compounds and compositions of the invention with blood allows further extension of the shelf life of blood and blood products.

Alternatives to Insulin and Glucose for Diabetics

Another metabolic disorder requiring maintenance of ATP levels is unavailability of glucose resulting from diabetes. In diabetes, glucose is not transported into cells and therefore is not utilized effectively for ATP production by the cells. Since glucose is a preferred fuel source for producing ATP, ATP levels fall. This dearth of ATP can result in or death.

The invention provides treatment for an individual in such a situation by delivering to the individual compounds and compositions of the invention as alternatives to glucose for producing ATP.

When insulin is used to stimulate glucose transport, blood glucose levels decrease as glucose is transported from the blood into the cells. When too much insulin is used, blood glucose levels may fall so much that patients may die from lapsing into an irreversible coma due to lack of glucose available to brain cells.

As an alternative to insulin treatment for providing fuel by stimulating glucose intake by the cells, the invention provides an alternative substrate fuel, for example, FBP, to replace glucose as the energy source. The patient can then be restored to a state of relative normalcy despite the failure of the tissues to take up a normal amount of glucose. This alternative treatment is preferable over insulin treatment, especially when insulin is ineffective (insulin resistance) to the point that the required insulin dose is either unacceptably high or more damaging than elevated glucose.

When an excess of insulin has been given, use of the alternative fuel sources and other ATP augmentation and maintenance compounds and compositions of the invention may be useful, optionally in combination with glucose, to prevent or reverse diabetic coma or to prevent or reverse clinical death associated with hypoglycemia due to the inadequacy of glucose by itself to generate energy with sufficient speed.

The amount of fuel source needed by an individual may be calculated by multiplying the normal glucose needed for healthy life by the stoichiometry described herein, (e.g., 1 or 0.5 for FBP, 1 or 2 for G3P, and 2 or 4 for PEP). The calculated amount of glucose equivalent thus determined is then delivered at a rate calculated to substitute for glucose over the pertinent time period.

Both insulin dependent and insulin resistant diabetics will be helped by the provision of the alternate fuels according to the invention.

Other Uses

Methods of the invention also provide for use of ATP augmentation and maintenance compounds and compositions of the invention of the invention compounds as dietary supplements for individuals who have chronic ischemic states, for example, pulmonary insufficiency (resulting from, for example, lung cancer, pulmonary edema, occupational exposure or aging), poor peripheral or cardiac circulation, or phlebitis. These methods can also be of value to other individuals who may simply feel fatigued. Compounds and compositions of the invention can be prepared as tablets, capsules, powders, liquids or in other dosage forms as dietary supplements and when desired may be enterically coated. Compounds and compositions of the invention may be provided in any suitable form for administration, as can be selected by one of ordinary skill in the art without undue experimentation. For example, they may be delivered orally, intravenously, intraperitoneally, intramuscularly or as suppositories in appropriate pharmaceutically acceptable carriers and forms.

During aging, cellular housekeeping does not keep up with the accumulation of damage to organelles and cells. Although age related defects in mitochondrial ATP production are not well defined, aging persons experience a sense of fatigue and lack of energy as their years progress. The invention alleviates aging effects in part by modulating ATP production to normal or supernormal levels. This stimulating effect should provide a generalized improvement in function which may combat a part of the generalized decline in functions characteristic in aging.

Another method of embodiments of the invention involves use of compounds and compositions of the invention for sports competitions. Sporting competitions may require maximal physical performance. A maximally exercising athlete will typically produce considerable lactic acid in his or her muscles, with a consequent fall in intracellular pH. This has an immediate effect of reduced performance and may also produce muscle soreness during days subsequent to exercising which may impact future training and/or performance. By ingesting or otherwise receiving compounds or compositions of the invention, for example, NAD+, FBP, G3P, 3-PG and/or PEP, prior to exercise, the athlete will be able to produce more ATP in relatively hypoxic and acidotic muscles than he or she could otherwise produce given the inhibition of glycolysis from decreased pH and subnormal oxygen tensions. The use of 3-PG and/or PEP by athletes may be particularly advantageous for preventing the accumulation of lactic acid in muscles when these agents are administered in sufficient dosage to compete with glucose as an energy source. The resultant decrease in lactate production will reduce lactate mediated muscle soreness and acid mediated performance limitations.

The invention also includes timed release dosage forms of ATP augmenting compounds, for example, FPB, G3P, 3-PG or PEP, especially for use in endurance sports, but also for other uses requiring continual metabolic support (including recovery from trauma, surgery, etc.). There are no known endogenous mechanisms for controlling blood levels of these compounds. Timed release dosage forms of the invention will provide steady levels of these compounds for a long duration of effectiveness. Timed release formulations may also be especially advantageous for treating diabetes or for treating effects of aging. Timed release formulations of pharmaceutical compounds and compositions are well known to those skilled in the art, and appropriate formulations can be selected and prepared without undue experimentation.

Dosages of the various cofactors used in the invention will vary depending on the form of delivery, for example, bathing, injecting or oral ingestion and permeabilities of the tissues to be treated. Effective amounts of ATP substrates and co-factors can be determined by routine experimentation similar to experiments in the examples in the instant application. Generally, intracellular concentrations of these factors of less than or equal to 50 µM will be effective. Depending on temperature and permeabilities of the compounds relative to the specific cell membrane, concentrations of each ATP substrate or cofactor may be adjusted for specific applications.

When a compound or composition of the invention is delivered in an oral or circulating form, blood or prefusate levels of the ATP substrates and co-factors will be adjusted to provide intracellular concentrations determined to be effective.

EXAMPLES

Example 1

Rabbit kidney cortical slices (0.5 mm thick) were kept anoxic (bubbled with 100% $N_2$ at pH 7.4) for 45 min, then were reoxygenated (100% $O_2$, pH 7.4) for 45 min and ATP content was determined. The substrates listed for each condition were the only ones available during both anoxia and hyperoxia. Table 1 shows that fructose 1,6-bisphosphate (FBP) is no more effective than glucose at enabling ATP synthetic capacity, perhaps because of the high pH of the anoxic medium, which may allow glycolysis to proceed without acid blockade. More importantly, G3P is as effective as either glucose or FBP despite being present at only 1/10th of its stoichiometrically comparative concentration, that is 20 mM or two times the FBP concentration. G3P is thus 5 times more effective than either glucose or FBP and 20 times as effective as pyruvate on a molar basis.

TABLE 1

| Substrate Available | Concentration | ATP Content (micromoles/mg wet weight) |
| --- | --- | --- |
| Glucose | 10 mM | 0.443 ± .019 |
| Fructose 1,6-bisphosphate | 10 mM | 0.431 ± .097 |
| Glyceraldehyde-3-phosphate | 2 mM | 0.437 ± .054 |
| Pyruvate | 40 mM | 0.420 ± .050 |

Example 2

In Example 2, pH was held at 7.0 and oxygen was not resupplied. The anoxic period was 60 min. This protocol allows ATP maintenance in the anoxic state to be examined directly at a pH closer to the low pH prevailing during complete anoxia in vivo; in vivo, access to exogenous substrate implies some circulation which implies a pH slightly higher than the 6.5–6.9 often seen with complete blockage of flow. In Table 2 results are expressed in micromoles ATP per mg of dry weight of the solid pellet spun down after homogenization of the tissue slices (rabbit kidney). The results again show that FBP is no better than glucose, that 2 mM G3P is approximately as effective as 10 mM glucose or 10 mM FBP, and that phosphoenolpyruvate (PEP) is by far more effective than either glucose or FBP when PEP is used at its proper stoichiometric concentration. The results from the combination of NAD$^+$ with G3P imply that NAD$^+$ may be inhibitory. However, this result is an artifact due to the particular assay used to measure ATP concentration. NAD$^+$ is a product of the reaction by which ATP is measured, and sufficient NAD$^+$ to inhibit the ATP detection reaction by endproduct inhibition was carried into the assay medium from the unwashed slices.

Separate experiments in which PEP was added to ATP in the ATP assay indicated no false detection of PEP as ATP, i.e., PEP does not produce a false positive assay for ATP. ATP production from pyruvate was surprisingly high, given that pyruvate is not a glycolytic fuel, but pyruvate, as expected, gave the lowest ATP yield of all substrates other than the artifactual result from G3P+NAD$^+$.

TABLE 2

| Substrate Available | Concentration | ATP Content (micromoles/mg dry pellet weight) |
| --- | --- | --- |
| Glucose | 10 mM | 0.465 ± .015 |
| Fructose 1,6-bisphosphate | 10 mM | 0.475 ± .005 |
| Glyceraldehyde-3-phosphate | 2 mM | 0.415 ± .0015 |
| G3P plus 20 mM NAD$^+$ | 2 mM | 0.300 ± .050 |
| Phosphoenolpyruvate | 40 mM | 0.720 ± .06 |
| Pyruvate | 40 mM | 0.345 ± .005 |

Example 3

The conditions of Example 3 were similar to those of Example 2, but 3-phosphoglycerate (3-PG) was used in place of pyruvate, and G3P concentration was raised to a stoichiometrically comparable value relative to FBP of 20 mm. Table 3 shows the results of Example 3, wherein for unknown reasons, the assay results are all low in comparison to the other examples. As expected from the first two experiments, G3P exceeds glucose in its ability to enable ATP production, the ATP content being about 70% higher than with glucose. Consistent with Example 2, NAD$^+$ gives the lowest apparent ATP content, again for artifactual reasons (interference with the assay). Also consistent with Example 2, PEP yields a higher ATP content than glucose, the PEP result being 52% higher than the glucose result. Also, 3-phosphoglycerate which has not been tested in the other examples, exceeds glucose-stimulated ATP by 22%. Inconsistent with Examples 1 and 2 is a finding that FBP now yields more ATP than glucose and, in fact, yields more ATP than PEP. Nevertheless, FBP does not consistently outperform glucose whereas PEP does; and G3P results showing an improvement over glucose when used at the proper stoichiometry are consistent with what would be expected based on its parity with glucose when used at drastically sub-stoichiometric concentrations. In summary, all substrates tested in Example 3 were more effective than glucose, provided NAD$^+$ did not disrupt the assay.

TABLE 3

| Substrate Available | Concentration | ATP Content (micromoles/mg dry pellet weight) |
| --- | --- | --- |
| Glucose | 10 mM | 0.115 ± .005 |
| Fructose 1,6-bisphosphate | 10 mM | 0.300 ± .02 |
| Glyceraldehyde-3-phosphate | 20 mM | 0.195 ± .005 |
| G3P plus 20 mM NAD$^+$ | 20 mM | 0.055 ± .009 |
| Phosphoenolpyruvate | 40 mM | 0.175 ± .015 |
| 3-Phosphoglycerate | 40 mM | 0.140 ± .020 |

Example 4

Example 4 shows that exposure to the test substrates improves ATP synthetic ability after reoxygenation. The conditions of Example 4 were similar to those of Example 3, except liver slices were used and the slices were transferred after a 60 min period of anoxia to the fresh oxygenated media that contained only glucose as the energy source. These conditions better simulate the in vivo state, in which the primary substrate available upon reoxygenation will be glucose. These conditions also allow NAD$^+$ to be tested under anaerobic conditions and then removed afterwards so as to avoid interference with the ATP assay. ATP was measured after 150 min of incubation in the presence of oxygen. The results are striking. Although the variability in the control group (glucose) is high, the mean ATP content in the glucose control group is higher than the mean for FBP, indicating that FBP provided no protection during 60 min of anoxia in comparison to glucose. In fact, the result for FBP is indistinguishable from the result for pyruvate, again indicating no protection by FBP. In contrast to these two conventional groups, all of the substrates of the present invention tested herein give mean ATP yields in excess of that obtained for glucose. As in Example 2, PEP outperforms G3P, although marginally. Most strikingly, the G3P+NAD$^+$ group gave ATP contents averaging 83% higher than the glucose group, and 49% higher than the G3P group without NAD$^+$, thus indicating that NAD$^+$ is indeed a highly effective additive for driving anaerobic ATP production. These NAD$^+$ results support our conclusion concerning the earlier technical difficulties of measuring effects of NAD$^+$.

TABLE 4

| Substrate Available | Concentration | ATP Content (micromoles/mg wet pellet weight) |
|---|---|---|
| Glucose | 10 mM | 0.333 ± .163 |
| Fructose 1,6-bisphosphate | 10 mM | 0.303 ± .099 |
| Glyceraldehyde-3-phosphate | 20 mM | 0.409 ± .054 |
| G3P plus 20 mM NAD$^+$ | 20 mM | 0.608 ± .002 |
| Phosphoenolpyruvate | 40 mM | 0.428 (n = 1) |
| Pyruvate | 10 mM | 0.292 ± .046 |

In summary, Examples 1 through 4 amply demonstrate that anaerobic substrates that have previously been used as glucose substitutes are not the most effective anaerobic substrates that can be used. Contrary to the known art, substrates other than FBP and pyruvate can yield higher ATP production during anaerobic and subsequent aerobic exposures than can FBP or pyruvate. These novel substrates support ATP production particularly well when combined with NAD$^+$.

While the invention has been described with reference to particular preferred embodiments, the invention is not limited to the specific examples given, and other embodiments and modifications can be made by those skilled in the art without departing from the spirit and scope of the invention.

What is claimed is:

1. A process for augmenting ATP production in an oxygen metabolism impaired tissue, comprising:
   administering to the tissue an effective amount of at least one exogenous compound selected from the group consisting of 3-PG, G3P, PEP, NAD$^+$, coenzyme A and acetyl coenzyme A.

2. A process according to claim 1, wherein the tissue is in a hypothermic state.

3. A process according to claim 1, further comprising administering exogenous pyruvate to the tissue.

4. A process according to claim 1, wherein said administering of said at least one compound follows administration of an anesthetic to said tissue, said at least one compound being administered in an amount of effective to reverse effects of said anesthetic.

5. A process according to claim 1, wherein the tissue is a blood product.

6. A process according to claim 1, wherein the tissue is in an individual suffering from a chronic ischemic state.

7. A process according to claim 1, wherein said tissue is mammalian tissue.

8. A process according to claim 7, wherein a mammal comprises said mammalian tissue and said at least one compound is administered to said mammal prior to exercise.

9. A process according to claim 1, wherein said administering is effected during a period when the tissue experiences ischemia or anoxia.

10. A process according to claim 9, wherein the tissue is part of a cryopreserved tissue and said administering is effective to produce ATP augmentation that assists in repairing cellular damage in said tissue.

11. A process according to claim 1, wherein said administering is effected before the tissue is subjected to an anticipated period of ischemia or anoxia.

12. A process according to claim 1, further comprising administering exogenous FBP to said tissue.

13. A process according to claim 1, wherein the at least one compound comprises NAD$^+$.

14. A process according to claim 1, wherein said at least one compound comprises NAD$^+$ and G3P.

15. A process according to claim 1, further comprising administering exogenous 2,3-DPG to said tissue.

16. A process according to claim 1, wherein said at least one compound comprises NAD$^+$, said process further comprising administering at least one to said tissue exogenous selected from the group consisting of FBP, G3P, 3-PG, PEP and pyruvate.

17. A process according to claim 1, wherein said at least one compound comprises NAD$^+$, said process further comprising administering exogenous 2,3-DPG to said tissue.

18. A process according to claim 1, wherein said at least one compound comprises NAD$^+$, and at least one of said coenzyme A and acetyl coenzyme A to said tissue.

19. A process according to claim 16, further comprising administering (i) said coenzyme A or said acetyl coenzyme A and (ii) exogenous carnitine or exogenous acetyl carnitine to said tissue.

20. A process according to claim 1, further comprising administering a pH buffer to said tissue in an amount effective to suppress an ischemia- or anoxia- associated pH decrease.

21. A process according to claim 20, further comprising administering an exogenous hydrogen ion transport inhibitor to said tissue.

22. A process according to claim 21, wherein said ion transport inhibitor comprises amiloride or dimethyl amiloride.

23. A process according to claim 1, wherein said at least one compound comprises NAD$^+$, said process further comprising adminsitering to said tissue exogenous 2-3-DPG and at least one exogenous compound selected from the group consisting of 3-PG, G3P and FBP.

24. A process according to claim 1, wherein said process comprises administering at least one exogenous compound for a purpose selected from the group consisting of: reducing or preventing tissue damage in acute or chronic ischemia, reversing anesthesia, treating diabetes, reversing or preventing coma, reversing processes of ageing, supplementing a diet, enhancing athletic performance, improving outcome of tissue transplantation or other surgery, mitigating at least one condition selected from the group consisting of ischemia, hypoxia and anoxia, and preserving cold stored or cryopreserved transplantable tissues.

25. A process according to claim 1, wherein said administering occurs before said tissue is metabolically impaired.

26. A process for mitigating damage due to an oxygen and/or fuel deficit in a cryopreserved organ, comprising:
   administering to the organ an effective amount of at least one compound selected from the group consisting of FBP, 3-PG, G3P, PEP, NAD$^+$, coenzyme A, acetyl coenzyme A, carnitine and acetyl-carnitine.

27. A process for treating a patient afflicted with a glucose metabolism defect, comprising:
   administering to the patient at least one compound selected from the group consisting of FBP, 3-PG, PEP, NAD$^+$, coenzyme A and acetyl coenzyme A in an amount effective to treat symptoms of said glucose metabolism defect.

28. A process according to claim 27, wherein said amount is effective to prevent or reverse diabetic coma or hypoglycemic associated clinical death.

29. A method for improving athletic performance, comprising administering to an individual before an athletic competition at least one compound selected from the group consisting of FBP, 3-PG, G3P, PEP, NAD$^+$, coenzyme A in an amount effective to augment ATP levels in said individual during said competition.

30. A method according to claim 29, wherein said at least one compound is administered in a timed release form.

31. A method for maintenance of ATP production in an individual comprising:

administering to said individual at least one compound according to claim 28, said individual internalizing said at least one compound and distributing said at least one compound to at least one tissue of said individual by at least one route selected from the group consisting of circulation, digestion and absorption through skin or membranes.

32. An ATP augmentation composition, comprising at least one compound selected from the group consisting of FBP, G3P, 3-PG, PEP, $NAD^+$, coenzyme A and acetyl coenzyme A in a timed release form.

33. A composition according to claim 32, wherein said composition is in a form suitable for oral administration.

34. A process for augmenting ATP production in an organ, comprising administering to said organ exogenous an effective amount of pyruvate and FBP.

35. An ATP augmentation composition comprising:

a pharmaceutically acceptable carrier; and at least one compound selected from the group consisting of 3-PG, PEP, and acetyl coenzyme A.

36. A composition according to claim 35, further comprising at least one compound selected from the group consisting of pyruvate G3P, $NAD^+$, coenzyme A, and FBP.

37. A composition according to claim 36, wherein said at least one compound comprises $NAD^+$ and a second compound selected from said group.

38. A composition according to claim 36, wherein said at least one compound comprises (i) $NAD^+$ and (ii) coenzyme A or acetyl coenzyme A, said composition further comprising carnitine or acetyl carnitine.

39. A composition according to claim 36, wherein said composition comprises (i) $NAD^+$, (ii) at least one compound selected from the group consisting of coenzyme A and acetyl coenzyme A, and (iii) at least one compound selected from the group consisting of G3P, 3-PG, PEP, pyruvate and FBP.

40. A composition according to claim 36, wherein said composition comprises (i) $NAD^+$, (ii) at least one compound selected from the group consisting of coenzyme A and acetyl coenzyme A, (iii) at least one compound selected from the group consisting of G3P, 3-PG, PEP, pyruvate and FBP, and (iv) at least one compound selected from the group consisting of carnitine and acetyl carnitine.

41. A composition according to claim 35, further comprising at least one member selected from the group consisting of carnitine and acetyl carnitine.

42. A process for treating or preventing energy deficit associated damage to a tissue in oxygen or fuel deficit by augmenting ATP production in said tissue, comprising:

administering to said tissue an effective amount of at least one exogenous compound selected from the group consisting of 3-PG, G3P, PEP, $NAD^+$, coenzyme A and acetyl coenzyme A.

43. An ATP augmentation composition comprising:

a carrier acceptable for pharmaceutical injection; and at least one compound selected from the group consisting of G3P, $NAD^+$ and coenzyme A.

* * * * *